United States Patent [19]

Bailey et al.

[11] 4,367,435
[45] Jan. 4, 1983

[54] MOTOR CONTROL SYSTEM

[75] Inventors: Wilber H. Bailey, Leucadia; Stephen J. Kreinick, San Diego; Bradley J. Denny, San Marcos, all of Calif.

[73] Assignee: Ivac Corporation, San Diego, Calif.

[21] Appl. No.: 216,762

[22] Filed: Dec. 15, 1980

[51] Int. Cl.³ .......................................... H02K 27/20
[52] U.S. Cl. ................................... 318/313; 318/258; 318/280; 318/269
[58] Field of Search ................... 318/139, 280, 281, 3, 318/10, 309, 326, 759, 760, 373, 275, 277, 256, 258, 272, 138, 254, 282, 258, 376, 602, 612, 685, 313, 696; 128/214 R, 230, 234, DIG. 1

[56] References Cited

U.S. PATENT DOCUMENTS

| | | | |
|---|---|---|---|
| 3,426,262 | 2/1969 | Colter | 318/313 |
| 3,746,958 | 7/1973 | Leenhouts | 318/138 X |
| 3,766,458 | 10/1973 | Nishimura et al. | 318/138 X |
| 3,914,677 | 10/1975 | MacWade et al. | 318/617 X |
| 4,087,732 | 5/1978 | Pritchard | 318/685 X |
| 4,191,187 | 3/1980 | Wright | 128/DIG. 1 |
| 4,228,396 | 10/1980 | Palombo et al. | 318/313 X |

*Primary Examiner*—Ulysses Weldon
*Attorney, Agent, or Firm*—Fulwider, Patton, Rieber, Lee & Utecht

[57] ABSTRACT

A digital servo control system for a d.c. motor to achieve stepping motor precision and a wider speed control range than either a conventional d.c. motor or a stepping motor, as may be typically utilized in an IV syringe pump. Motor position and direction sensing, as well as motor advance signals at the desired motor rate, condition motor advance and retard logic which, in turn, effects a unique counter-controlled motor drive subsystem to cause the d.c. motor to move forward, reverse, coast or slow down over a 1,000 to 1 speed control range.

14 Claims, 40 Drawing Figures

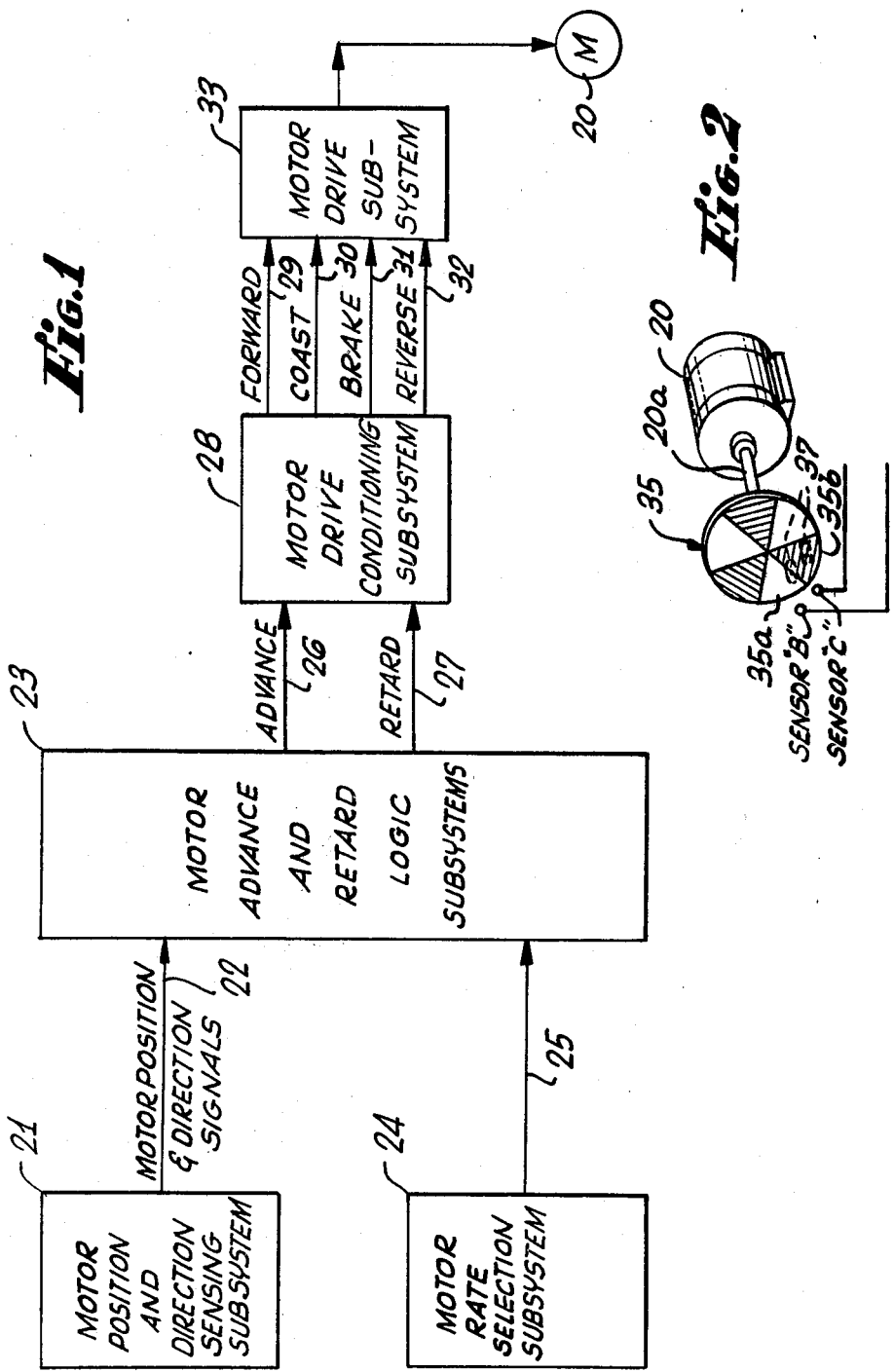

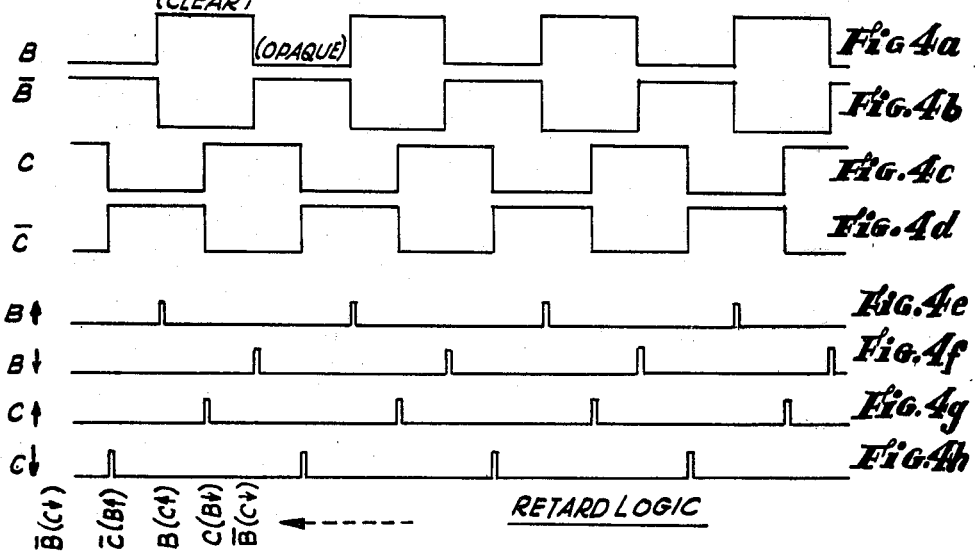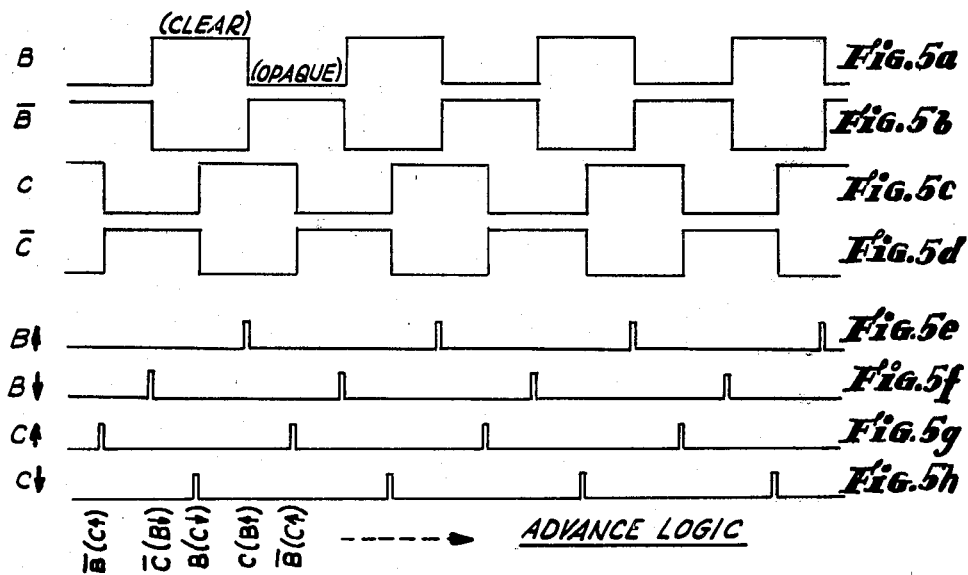

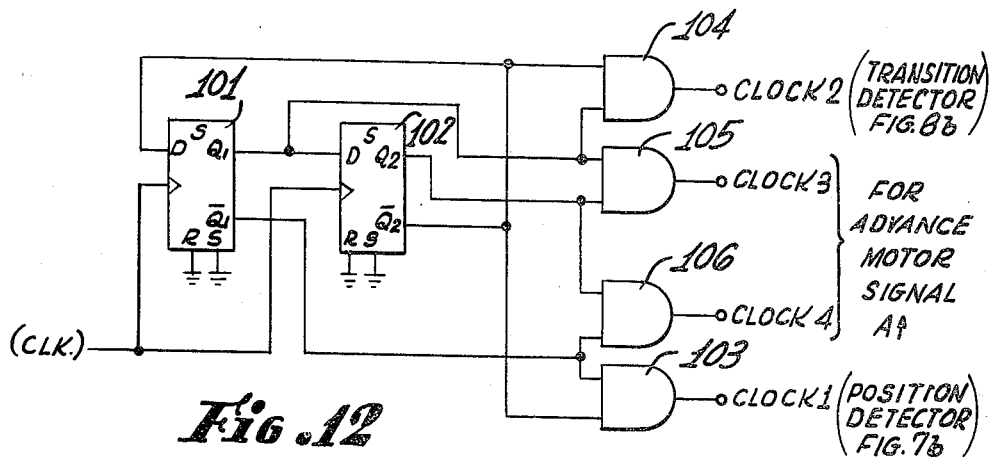

MOTOR CONTROL SYSTEM

BACKGROUND OF THE INVENTION

This invention relates generally to improvements in motor control systems and, more particularly, to a new and improved digital servo motor control system for a d.c. motor to render such a motor suitable for use in a syringe pump for parenteral administration (referred to herein as "intravenous administration" or "IV administration") of medical fluids over an extremely wide range of fluid flow rates, whereby high speed d.c. motor and low speed stepping motor performance is achieved, with stepping motor precision, yet in a more compact, lightweight, lower cost arrangement requiring less power and fewer electrical components.

The usual medical procedure for the gradual IV administration of fluids into the human body, such as fluid replacement, liquid nutrients, blood or plasma, makes use of apparatus which is commonly referred to in the medical arts as an intravenous solution administration set. Such a set typically is a disposable plastic product, and comprises a drop chamber adapted to be connected to a fluid source, a length of tubing extending from the chamber to the patient and a valve mechanism, such as a roller clamp on the tubing.

The drip chamber of the IV administration set serves a dual function of allowing a nurse or other attendant to observe the rate at which the fluid drips out of the fluid source and also creates a reservoir for the fluid at the lower end of the drip chamber to insure that no air enters the main feeding tube leading to the patient.

While observation of the rate of drop flow via the drip chamber is a simple way of controlling the amount of fluid fed to a patient over a period of time, its ultimate effectiveness requires that a relatively constant vigil be maintained on the drop flow, lest it cease entirely due to exhaustion of the fluid supply or vary unacceptably from the set rate.

In addition to the aforedescribed difficulties, the IV administration of medical fluids by gravity induced hydrostatic pressure infusion of the liquid from a fluid source suspended above a patient, may be susceptible to fluid flow rate variations due to changes in the fluid level in the bottle, changes in temperature, changes in the venous or arterial pressure of the patient, patient movement, and drift in the effective setting of the roller clamp or other valve mechanism pinching the feeding tube. Moreover, there are a number of situations, such as in intensive care, cardiac and pediatric patients, or where rather critical drugs are being administered, where the desired drop flow rate must be capable of rather precise selection and must not drift beyond certain prescribed limits in spite of varying load conditions.

In view of the foregoing, a number of electrical monitoring systems, drop flow controllers and infusion pumps have been developed in recent years to infuse medical fluids into patients at precisely regulated fluid flow rates. However, while such devices have generally served their purpose, there is a continuing need for improvement in accuracy and precision of adjustment over a wide range of selected flow rates. In this regard, difficulties have been experienced in connection with establishing and maintaining such accurate fluid flow rates at the extreme ends of the operating range, i.e., at very high flow rates and very low flow rates over a wide flow rate range such as 1,000 to 1, and there has been a desire to reduce the size, weight and complexity of the infusion devices without any reduction in accuracy and reliability.

Syringe pumps have been developed and have become popular in the IV administration of fluids into the human body, such syringe pumps typically embodying a motor driving a piston within a syringe to expel fluid from the syringe at a controlled rate through a length of tubing and into the patient. In the past, such syringe pumps have commonly used relatively bulky and expensive stepping motor drives which require holding current circuits, ramp up/ramp down circuits and special mechanical coupling techniques to obtain wide operating speed ranges. In addition, the torque characteristics of typical stepping motors tend to vary with speed and introduce additional difficult design problems, and stepping motors typically cannot provide adequate high speed performance.

While d.c. motors offer lower power consumption and higher speed performance, in a more compact, lightweight, structural arrangement, such d.c. motors lack the low speed performance and precision of stepping motors. In this regard, conventional d.c. motors tend to overshoot and undershoot with changing loads and speeds rather than moving in precisely commanded increments of motion. In addition, d.c. motor drive circuits may require digital-to-analog conversion hardware and torque control circuitry, which increases power loss and circuit complexity. Moreover, temperature and voltage variations can decrease speed control accuracy with conventional d.c. motors.

Hence, those concerned with the development and use of motor control and drive systems of the type suitable for use in IV fluid administration systems, and particularly those concerned with the design of IV syringe pumps, have long recognized the need for improved, relatively simple, economical, compact, reliable, lightweight, stable and accurate devices, including improvements in motor control systems for effectively accomplishing a wider motor speed control range and a concomitant wide range of precisely delivered fluid flow rates, in order to obviate the aforedescribed difficulties. The present invention clearly fulfills this need.

SUMMARY OF THE INVENTION

Briefly, and in general terms, the present invention provides a new and improved method and apparatus for very accurately controlling a d.c. motor over an extremely wide speed control range, to achieve stepping motor precision and a wider speed control range than either a stepping motor or a conventional d.c. motor, and thereby being capable of use in a precision syringe pump for parenteral administration of medical fluids accurately over an extremely wide range of fluid flow rates.

In the system of the present invention, motor position and direction sensing, as well as motor advance signals at the desired motor drive rate, condition appropriate motor advance and retard logic subsystems which, in turn, alter the state of a unique counter-controlled motor drive subsystem to cause a d.c. motor to move forward, reverse, coast or slow down over a very wide, typically 1,000 to 1, speed control range. The d.c. motor drive utilized in the digital servo motor control system of the present invention is a modified H-drive providing the additional capability of coasting and slow down modes of operation, as well as the normal forward and reverse operational states.

By way of example, the unique H-drive used in the system of the present invention employs solid state switching devices conditioned by "forward" and "reverse" signals and logical complements of these signals in various combinations to not only drive the d.c. motor in the forward and reverse directions of rotation by controlling the direction of current flow through the motor, but also provide the capability of open circuiting the motor to establish the coast mode, as well as the capability of effectively shorting out the motor to establish a slow down or braking mode of operation. These four digital servo control states, i.e., forward, coast, slow down and reverse, are selectively utilized to precisely regulate motor speed over a wide speed control range, even in the face of widely varying load and speed change conditions, and are effective in overcoming both overshoot and undershoot conditions that might otherwise occur in the absence of such control.

In one embodiment of the invention, by way of example and not by way of limitation, a combination of opto-electronic sensing for motor position and direction of movement provides signals, together with a source of motor advance signals at a selected motor rate, to condition motor advance and retard logic. The advance logic is responsive to all logical combinations of signals indicating that a reverse movement of the d.c. motor has actually occurred or that a forward movement of the motor has been requested, whereas the retard logic is responsive to all logical combinations indicating that a forward movement of the motor has actually occurred. The motor advance and retard logic subsystems drive an up/down counter subsystem or the equivalent which is a measure of the motor state in terms of where the motor should go relative to where the motor has actually gone. The state of the counter subsystem, which is in essence a digital meter for the performance of the motor, relative to the commanded motor rate which has been selected, is decoded to provide appropriate "forward" and "reverse" signals for the H-drive so that the d.c. motor performs with stepping motor precision over a much wider speed range than a typical stepping motor or a conventional d.c. motor, over widely varying load conditions.

The new and improved digital servo motor control system of the present invention, suitable for use as the motor drive in an IV syringe pump, is extremely accurate, reliable and easy to use in selecting and maintaining fluid flow rates over an extremely wide operational range, in a system which is more compact, less expensive, requires fewer electronic components and has lower power requirements.

These and other objects and advantages of the invention will become apparent from the following more detailed description, when taken in conjunction with the accompanying drawings of illustrative embodiments.

BRIEF DESCRIPTION OF THE DRAWINGS

FIG. 1 is a block diagram or flow chart for a motor control system in accordance with the present invention;

FIG. 2 illustrates the opto-electronic sensing system for motor position and direction of motion;

FIGS. 4a–4h are waveforms illustrating the operation of the motor position and direction sensing subsystem for forward movement of the motor;

FIGS. 5a–5h are waveforms, similar to those of FIGS. 4a–4h, illustrating the operation of the motor position and direction sensing subsystem for reverse movement of the motor;

FIG. 12 illustrates suitable logic for generating a 4-phase clock useful in the practice of the invention;

FIGS. 13a–13g are timing diagram waveforms to illustrate the operation of the logic shown in FIG. 12;

DESCRIPTION OF THE PREFERRED EMBODIMENT

Figure 3:
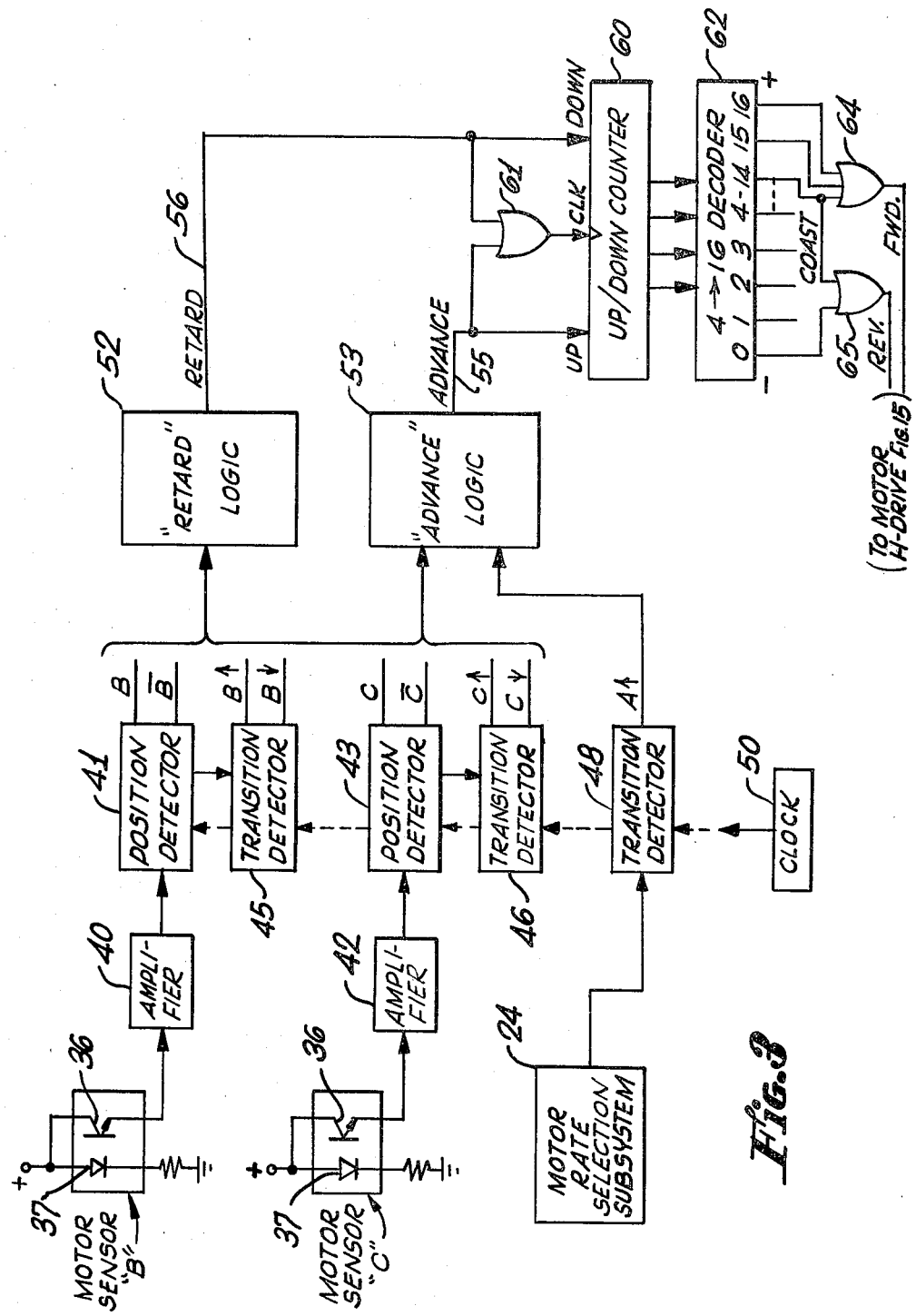
FIG. 3 is a more detailed block diagram of the digital servo control system of the present invention, exclusive of the details of the modified H-drive.

Referring now to FIG. 1 of the drawings, there is shown a new and improved motor drive and control system, emobodying features of the present invention. Although reference has been made in the previous description of the intravenous administration environment, and particularly to syringe pumps, for which the unique motor drive and control system of the present invention was specifically developed, it is to be understood that this is by way of example only, and the digital servo control system for a d.c. motor set forth in the ensuing description is also suitable for use in other environments and for a wide variety of applications other than intravenous administration. In addition, while the preferred method and architecture of the motor control system of the present invention is illustrated in a hardware logic format for convenience in describing the basic structure and operation of the invention, it is to be understood that this is also by way of example only and not by way of limitation, and the same or equivalent structure and operation may be appropriately implemented in software by a suitably programmed microprocessor or the like, or as a combination of software and hardware, without in any way departing from the spirit and scope of the present invention.

FIG. 1 is a system block diagram or flow chart, capable of implementation by either hardware or software, and illustrates a basic digital servo drive and control system, in accordance with the invention, for a d.c. motor 20 which achieves stepping motor precision and a wider speed control range than either a conventional d.c. motor or a stepping motor over widely varying load and speed change conditions. Typically, when a driving pulse is directed as input to a stepping motor, the stepping motor responds by moving a single precisely defined discrete step or increment of movement, with neither overshoot nor undershoot. In contrast, there are no individual, discrete steps of motion which occur with a conventional d.c. motor. Once energized, such a d.c. motor will overcome its inertia and friction and continue in motion until it is stopped electrically and/or by friction. Hence, such d.c. motors tend to overshoot and undershoot under varying load and speed change conditions.

In the system of the present invention, means are provided for monitoring the position and motion of the motor, to keep track of how far the motor has gone and, if it is going too far, relative to where it has been commanded to go, to slow it down. Indeed, under conditions of sufficient overshoot, where the motor has gone much too far from where it should be, the system provides means for stopping the motor and even driving it in reverse, so that the trend of its motion will compensate for its overshoot and undershoot characteristics and more closely simulate, over a long time average, quasi-stepping motor precision of movement.

The present invention accomplishes the foregoing by establishing and combining into a hierarchy four modes of operation in which the system of the present invention is capable of placing the d.c. motor. These four modes of operation are forward movement, coasting, slowing or braking of the motor, and reverse movement, and the system can selectively utilize these states in any combination and sequence to rapidly control motor movement so that it precisely tracks the selected motor rate with minimal overshoot and undershoot. By way of example, the motor 20 may be electrically energized and requested to advance by 2 increments of movement as established by a pair of motor advance signals. If, however, the motor overshoots and moves by 3 increments, then the motor may be placed in the "coast" state until the system has caught up so that the commanded movement and the actual movement are again in step. The system may switch back and forth between "forward" and "coast" modes in any order and for as long as necessary to accomplish proper motor movement. If, however, the load on the motor 20 suddenly reduces to a substantial degree, the motor may overshoot to a much greater degree than can be compensated for rapidly by the "coast" state alone. Under such circumstances, the motor may be switched to the slow down or braking mode as well as the "forward" and "coast" modes, in order to more rapidly bring the motor movement back to where it should be. In extreme cases, e.g., where the motor is moving at a relatively high speed and the selected motor rate is suddenly changed to a much lower rate, so that very substantial overshoot may occur, then the system of the present invention is capable of actually driving the motor backwards by switching to the "reverse" mode of operation in the system hierarchy of commands.

In the system of FIG. 1, a motor position and direction sensing subsystem 21 senses the actual position and direction of movement of the motor 20 by any appropriate means, such as an opto-electronic sensing apparatus more fully described hereinafter, and directs such motor position and direction signals over line 22 to motor advance and retard logic subsystems 23.

A suitable motor rate selection subsystem 24, in either hardware or software, establishes a pulse train (or a waveform from which a pulse train can be derived) which represents the desired motor rate and directs a plurality of periodically occurring advance motor signals over line 25 to the motor advance and retard logic subsystems 23.

The motor advance amd retard logic subsystems 23 evaluate the signal inputs from the sensing subsystem 21 and rate selection subsystem 24 to generate appropriate "advance" and "retard" signals over lines 26, 27, respectively, to a motor drive conditioning subsystem 28. The advance logic subsystem is responsive to all logical combinations of signals from the sensing subsystem 21 and rate selection subsystem 24 which indicate that a forward movement of the motor has been requested or that a reverse movement of the d.c. motor has actually occurred, the latter being an indication of negative motor movement which must be made up or compensated by additional subsequent forward motion. In other words, actual backward motion is considered equivalent to a command to go forward in order to make up for such reverse movement.

The retard logic in the subsystem 23 is responsive to all logical combinations of input signals indicating that a forward movement of the motor has actually occurred.

The "advance" and "retard" signals, directed over lines 26 and 27, alter the state of a motor drive conditioning subsystem 28, which is typically an up/down counter subsystem keeping track of motor performance in terms of where the motor should go relative to where the motor has actually gone. The subsystem 28 operates between extremes indicating an excess of actual forward motion on one hand and an excess of commands to go forward (or the eqivalent in actual reverse movement) that have not been executed, on the other hand.

The continuously updated accumulation of offsetting "advance" and "retard" signals is decoded to provide appropriate "forward", "coast", "brake" and "reverse" output command signals over lines 29-32, respectively, to a motor drive subsystem 33 which utilizes such signals to vary the state of operation of the motor 20 so that the d.c. motor performs with quasi-stepping motor precision over a much wider speed range than a typical stepping motor or a conventional d.c. motor and over widely varying load conditions.

As best observed in FIG. 2, the opto-electronic sensing for motor position and direction of movement may be accomplished by an optical disc 35 which is typically located on the same shaft 20a as the motor drive shaft for the d.c. motor 20, the disc having a plurality of alternating light and dark (typically clear and opaque) sectors 35a, 35b, respectively, of uniform size and spacing spread over the entire 360° of a single complete disc rotation.

The clear and opaque sectors 35a, 35b are monitored by a pair of opto-electronic sensors B and C, each sensor comprising a phototransistor light detector 36 and a suitable light source 37 such as a light emitting diode (LED) located on opposite sides of the disc, so that the light beam from the LED is modulated by the rotating disc and sensed by the phototransistor detector.

The pair of sensors B and C are physically spaced apart from each other, along equal radii from the center of the disc 35, by a distance of ½ sector, so that the sensors are in phase quadrature relative to a full cycle consisting of a pair of consecutive clear and opaque sectors. The sensors B and C can readily detect the abrupt transitions between clear and opaque sectors and optically discriminate motor position and direction to within ½ of a single disc sector.

Referring now to FIG. 3 of the drawings, there is shown a more detailed block diagram of the digital servo control system of the present invention, for monitoring motor position and direction and generating command signals for the motor drive subsystem. Motor sensors B and C in FIG. 3 correspond to the sensors previously described in connection with the sectored disc 35 in FIG. 2.

The electrical output from the motor sensor B is amplified, via amplifier 40, and directed as input to a position detector 41. Similarly, the electrical output from the motor sensor C is amplified by the amplifier 42 and directed as input to a second position detector 43.

The position detectors 41 and 43 simply indicate by their output whether each sensor sees a clear or opaque sector area. Hence, the electrical output from the position detector 41 is a pair of signals B and $\overline{B}$. The B signal will be high or "true" when the motor sensor B is opposite a clear sector of the disc 35 in FIG. 2, and the B output will be low or "false" when the motor sensor B sees an opaque area of the disc. The $\overline{B}$ signal is simply the inverse or logical complement of the B signal. For purposes of subsequent explanation, the "true" or high state may be considered as a binary "1", while the "false" or low state may be considered a binary "0".

Similarly, the position detector 43 for the motor sensor C provides output signals corresponding to C and $\overline{C}$.

The electrical output of the position detector 41, i.e., signals B and $\overline{B}$, are also provided as input to a transition detector 45. Similarly, the C and $\overline{C}$ signals, from the position detector 43, are directed as input to a second transition detector 46.

Each of the transition detectors 45, 46 indicates whether or not its associated motor sensor has detected a transition from a clear sector to an opaque sector of the disc 35, or a transition from an opaque sector to a clear sector. Hence, the transition detector 45 provides a pair of electrical outputs in the form of signals B ↑ and B ↓. The B ↑ signal indicates that the motor sensor B has monitored a change in the rotating disc 35 from a clear sector to an opaque sector. The B ↓ signal indicates that the motor sensor B has seen a change from an opaque sector of the disc 35 to a clear sector. Correspondingly, the C ↑ output from the transition detector 46 indicates detection by the motor sensor C of a sudden transition from a clear sector to an opaque sector, while the C ↓ signal indicates a transition from an opaque sector to a clear sector.

As previously pointed out, the motor sensor B and motor sensor C are in phase quadrature, so that the B and C signals are spaced apart by ½ of a single disc sector. In addition, every ½ sector of the motor disc is a single motor step represented by the period between advance motor signals A ↑. These A ↑ signals are provided at the output of a transition detector 48, responsive to transitions in the repetitive waveform produced by the motor rate selection subsystem 24, to produce pulse output. Hence, the resolution of the motor control system is ½ of a disc sector.

A suitable clock 50 clocks all of the position detectors and transition detectors to insure synchronous operation.

The advance motor signals A ↑, position signals B, $\overline{B}$, C, $\overline{C}$ and transition signals B ↑, B ↓, C ↑, C ↓ are used to optically discriminate motor position and direction of movement and to assess performance of the motor in terms of where the motor has gone relative to where the motor should be. By monitoring this information continuously, an indication is provided regarding how far the motor has gone in either direction and its position at any time. This can be compared with information regarding where the motor should be, as indicated by an accumulation of motor advance signals A ↑. However, the nature of conventional d.c. motors, in terms of speed variation with changing load, means that overshoot and undershoot will occur with sudden variations in load. Accordingly, the control system keeps track of how much too far (overshoot) or too little (undershoot) the motor has gone and seeks to adjust the motor position to the desired state by the appropriate combination of "forward", "coast", "brake" and "reverse" command states to the motor drive system.

The electrical output of the position detectors 41, 43 and transition detectors 45, 46 are directed as input to a "retard" logic subsystem 52 and to an "advance" logic subsystem 53. The advance logic subsystem 53 also receives as an additional input the advance motor signals A ↑.

As previously indicated, the advance logic subsystem 53 is responsive to all logical combinations of signals indicating that a reverse movement of the d.c. motor 20 has actually occurred or that a forward movement of the motor has been requested, whereas the retard logic subsystem 52 is responsive to all logical combinations of signals indicating that a forward movement of the motor has actually occurred.

The Boolean equations for the advance logic and the retard logic are set forth below:

ADVANCE
LOGIC = $\overline{C}$(B ↓) + C(B ↑) + B(C ↓) + $\overline{B}$(C ↑) + A ↑

RETARD
LOGIC = C(B ↓) + $\overline{C}$(B ↑) + B(C ↑) + $\overline{B}$(C ↓)

The above equations indicate that there are four conditions of the motor sensors B and C that indicate the motor 20 has moved in reverse 1 step requiring compensatory forward motion, i.e., by ½ of a motor disc sector. These combinations of conditions are either a $\overline{C}$B ↓, or a CB ↑, or BC ↓, or $\overline{B}$C ↑. In addition, the advance motor signal A ↑ is included in the list of signals and signal combinations calling for forward motion of the motor 20. All of these conditions are ORed by the advance logic subsystem 53 and passed as an output "advance" signal over line 55. Similarly, there are four conditions of the motor sensors which indicate that the motor 20 has actually moved forward by a single step. These conditions are represented by a CB ↓ signal, or $\overline{C}$B ↑, or BC ↑, or $\overline{B}$C ↓. All of these signals are ORed by the retard logic subsystem 52 and passed as a output "retard" signal over line 56.

The motor advance and retard logic subsystems 53, 52 drive an up/down counter subsystem or the equivalent which is a measure of the motor state in terms of where the motor 20 should go relative to where the motor has actually gone. The state of the counter subsystem, which is in essence a digital meter for the performance of the motor 20, relative to the commanded motor rate which has been selected by the subsystem 24, is decoded to provide appropriate "forward" and "reverse" signals, and the complements of those signals, for a modified H-drive, so that the d.c. motor 20 performs with stepping motor precision over a wider speed range, typically, 1,000 to 1, than a typical stepping motor or a conventional d.c. motor, over widely varying conditions.

FIGS. 4a–4h illustrate, for forward movement of the motor 20, the signal waveforms which are directed as input to the retard logic subsystem 52, from which appropriate position and transition combinations are selected to generate the "retard" signals. FIG. 4a is a waveform for the B signal output from the position detector 41 as the disc 35 rotates clockwise in FIG. 2, indicating movement of the waveforms from left to right in FIG. 4. FIG. 4b is a similar waveform of the B̄ signal, which is the complement of the B signal and is, therefore, 180° out of phase with the B signal.

FIG. 4c and FIG. 4d are similar waveforms for the C and C̄ signals received from the position detector 43 for the motor sensor C. The C signal is out of phase with the B signal by ½ sector or 90°.

FIGS. 4e and 4f are waveforms of the B ↑ and B ↓ signals from the transition detector 45, while FIGS. 4g and 4h are similar waveforms for the C ↑ and C ↓ transition signals from the transition detector 46.

Referring to FIGS. 4a–4h collectively, it will be readily apparent that the waveforms verify the aforedescribed Boolean equation for the ORed retard logic signal conditions for generating an output "retard" signal over line 56 in FIG. 3. In this connection, the signal combinations are read off in sequential order upon the occurrence of any transition signal. Hence, the signal combination at the first transition in B̄(C ↓ ). Next in order is the C(B ↓ ). These four signal combinations repeat cyclicly in sequential order and are the only four signal combinations defining actual forward movement of the motor 20.

FIGS. 5a–5h correspond to FIGS. 4a–4h and illustrate the signal waveforms from the position detectors and the transition detectors for reverse motor movement, indicating counterclockwise motor rotation and movement of the waveforms from right to left in FIG. 5.

It will be apparent, in considering FIGS. 5a–5h collectively, that the previously described Boolean equation for the "advance" logic is verified by the signal combinations existing at the various sequentially occurring transitions. In this regard, at the first transition shown in FIG. 5g, the signal combination is B̄(C ↑ ). At the next transition in FIG. 5f, the signal combination is C̄(B ↓ ). The next transition in sequence occurs in FIG. 5h and is a B(C ↓ ) signal combination, while the next transition in FIG. 5e is a C(B ↑ ) signal combination. Again, these are the only four states indicating reverse movement of the motor 20, and they will repeat sequentially in the waveforms of FIGS. 5a–5h.

Referring now again to FIG. 3, the "advance" signals over line 55 and "retard" signals over line 56 step an up/down counter 60 either up or down, respectively, through an OR gate 61 which clocks the counter. The counter 60 is typically a binary counter with 4 line output. A 4 to 16 line decoder 62 converts the output of the counter 60 to 16 lines. While 16 output states from the decoder 62 are illustrated in FIG. 3, this is to be considered by way of example only, and any number of counter states may be decoded out in either hardware or software to monitor motor performance.

As shown for purposes of illustration, counts 15 and 16 at the high end of the decoder 62 are directed as inputs to a "forward" NOR gate 64. Hence, if either of the counter states 15 and 16 are activated, only the "forward" output is provided to the motor H-drive.

Under those circumstances, the output of the "forward" gate 64 would be a "0", while the output of the "reverse" NOR gate 65 would be a "1". As will subsequently be apparent, a "forward" "0" state combined with a "reverse" "1" state conditions the motor 20 to move forward.

If counter state "14" is activated, it provides an input to both of the NOR gates 64 and 65, so that both gates have a "0" output which defines a "coast" mode of operation for the motor 20. All of the other counter states "1" through "13" are shown connected to nothing, so that the inputs into and outputs from the "forward" and "reverse" gates 64, 65, respectively, are "1", which defines a dynamic braking or slowdown mode of operation for the motor 20. If the "0" decoder state is activated, then the "reverse" gate 65 provides a "0" output while the output of the "forward" gate 64 is "1", which defines a common signal combination for driving the motor 20 in reverse. Since only one of the decoder outputs is enabled at any one time, the output pattern from the decoder can be suitably tailored by any selective choice of jumpers to provide any type of motor performance desired using the 4-state hierarchy of forward, coast, braking and reverse movement of the motor 20.

Hence, the "advance" and "retard" signals over lines 55 and 56 alter the state of the counter 60 and decoder 62 which keep track of motor performance in terms of where the motor should go relative to where the motor has actually gone. The decoder 62 operates between extremes indicating an excess of actual forward motion, on the one hand, and, on the other hand, an excess of commands to go forward (or the equivalent in actual reverse movement) that have not been executed. The continuously decoded "forward", "coast", "brake" and "reverse" output command signals to the motor H-drive vary the state of operation of the motor 20 so that the d.c. motor performs with quasi-stepping motor precision over a much wider speed range than a typical stepping motor or a conventional d.c. motor.

Figure 6A:
FIGS. 6a and 6b illustrate a suitable amplifier circuit for practice of the invention.
Figure 6B:
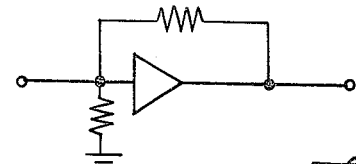

FIGS. 6a and 6b illustrate a suitable amplifier circuit for the amplifiers 40, 42 in FIG. 3. In this regard, the amplifier is shown in FIG. 6b as a conventional C-MOS logic amplifier, typically a C-MOS Type 4050 non-inverting buffered gate manufactured by R.C.A. Corp., Somerville, N.J.

Figure 7A:
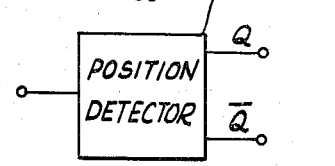
FIGS. 7a and 7b illustrate suitable position detection logic.
Figure 7B:
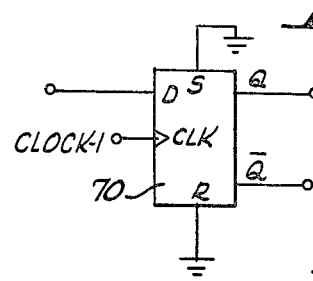

FIGS. 7a and 7b illustrate suitable logic for the position detectors 41, 43 in FIG. 3. FIG 7b illustrates a D-flip-flop 70 which latches depending upon whether or not the motor sensor associated with that position detector has seen a clear sector or an opaque sector of the disc 35. The clocking input to the flip-flop 70 is clocked repetitively by a clock 1 signal input at regular intervals. If the motor sensor sees a clear sector, then the input to the D terminal of the flip-flop will go high and, accordingly, on the next clock 1 signal, the "Q" output of the flip-flop (which corresponds to either B or C depending upon which position detector is involved) will also go high. Alternatively, if the motor sensor sees an opaque sector of the disc 35, the D input will be low and, therefore, the Q̄ output will go high on the next clock pulse.

Figure 8A:
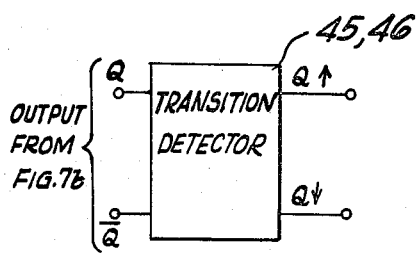
FIGS. 8a and 8b illustrate suitable transition detection logic.
Figure 8B:
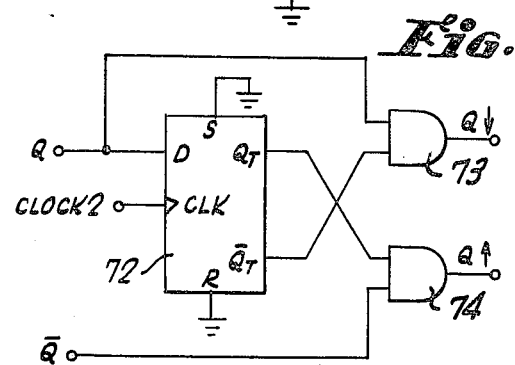

FIGS. 8a and 8b illustrate suitable logic for the transition detectors 45, 46 in FIG. 3. The transition detector receives as inputs to another D flip-flop 72 the Q and Q̄ outputs from the position detector flip-flop 70 of FIG. 7b. The D flip-flop 72, together with a pair of AND gates 73, 74 provide an output which indicates whether the input to the flip-flop has changed, so that a Q ↑ signal will be provided if the motor position sensor observation changes from a clear sector to an opaque sector, whereas a Q ↓ output will be provided if the area monitored by the sensor changes from an opaque sector to a clear sector.

The clocking input to the flip-flop 72 is clocked repetitively by a clock 2 signal input at regular intervals. In order to avoid confusion with the Q and $\overline{Q}$ outputs of the position detector flip-flop 70 in FIG. 7b, the outputs of the transition flip-flop 72 in FIG. 8b have been labeled $Q_T$ and $\overline{Q}_T$.

Assuming that the position sensor is opposite a clear sector, the Q output from the flip-flop 70 which is directed as input to the flip-flop 72 and the AND gate 73 will be high, whereas the $\overline{Q}$ input, directed only as as an input to the AND gate 74, will be low. At the next clock 2 pulse, the $Q_T$ output of the flip-flop 72 will go high and $\overline{Q}_T$ will go low. As a result, neither of the AND gates 73, 74 will be enabled and, therefore, both Q ↑ and Q ↓ (which corresponds to either B ↑ and B ↓ or C ↑ and C ↓ depending upon which motor sensor is involved) will be both be low since there is no output from the AND gates.

Assuming now that a transition has occurred before the next clock 1 pulse, so that the motor sensor now sees an opaque sector, Q will go low and $\overline{Q}$ will go high at the next clock 1 pulse in FIG. 7b. At this point, both inputs to the AND gate 74 in FIG. 8b will be high, so that a Q ↑ output will be provided to indicate a transition from a clear sector to an opaque sector. The Q ↓ output from the AND gate 73 will, of course, remain low since the Q input to the gate 73 and $\overline{Q}_T$ input are both low. When the next clock 2 pulse arrives, $Q_T$ will go low and $\overline{Q}_T$ will go high, thus terminating the Q ↑ output from the gate 74. Hence, the pulse width of the Q ↑ signal, which originates with a clock 1 pulse and terminates with a clock 2 pulse, is the time between the pair of clock pulses.

Similarly, if the motor sensor now detects a change from an opaque sector to a clear sector, Q will go high and $\overline{Q}$ will go low, so that a Q ↓ output will be provided from the AND gate 73 at the clock 1 pulse in FIG. 7b and will be terminated by the clock 2 pulse to the flip-flop 72 in FIG. 8b.

Figure 9A:
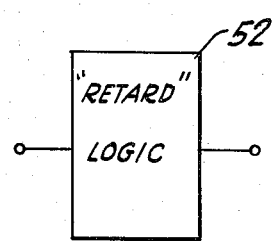
FIGS. 9a and 9b illustrate suitable retard logic for use in practicing the present invention.
Figure 9B:
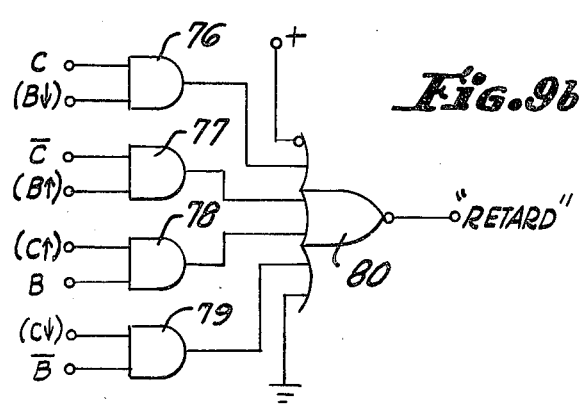

Referring now to FIGS. 9a and 9b, suitable logic is illustrated for the retard logic subsystem 52 in FIG. 3. Each of the four combinations of signals previously described in connection with the Boolean equation for actual forward movement of the motor 20 is directed as input to the appropriate one of four AND gates 76–79, and the outputs from all of these AND gates are fed as inputs to the OR gate 80 to provide an appropriate "retard" signal output whenever one of the prescribed signal combinations (as previously derived from the waveforms of FIGS. 4a–4h) has occurred.

Figure 10A:
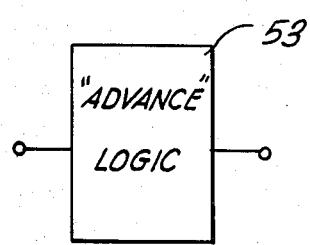
FIGS. 10a and 10b illustrate suitable advance logic for practicing the invention.
Figure 10B:
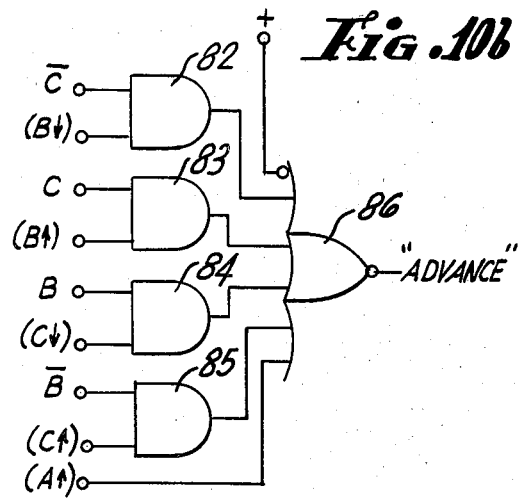

Similarly, FIGS. 10a and 10b illustrate suitable logic for the advance logic subsystem 53 in FIG. 3. Again, four AND gates 82–85 receive as their respective inputs the various signal combinations which prescribe the generation of an "advance" signal. The outputs of all of the AND gates 82–85, together with the advance motor signal A ↑, are fed to an OR gate 86 which provides the appropriate output "advance" signal whenever any of its inputs go high.

Figure 11:
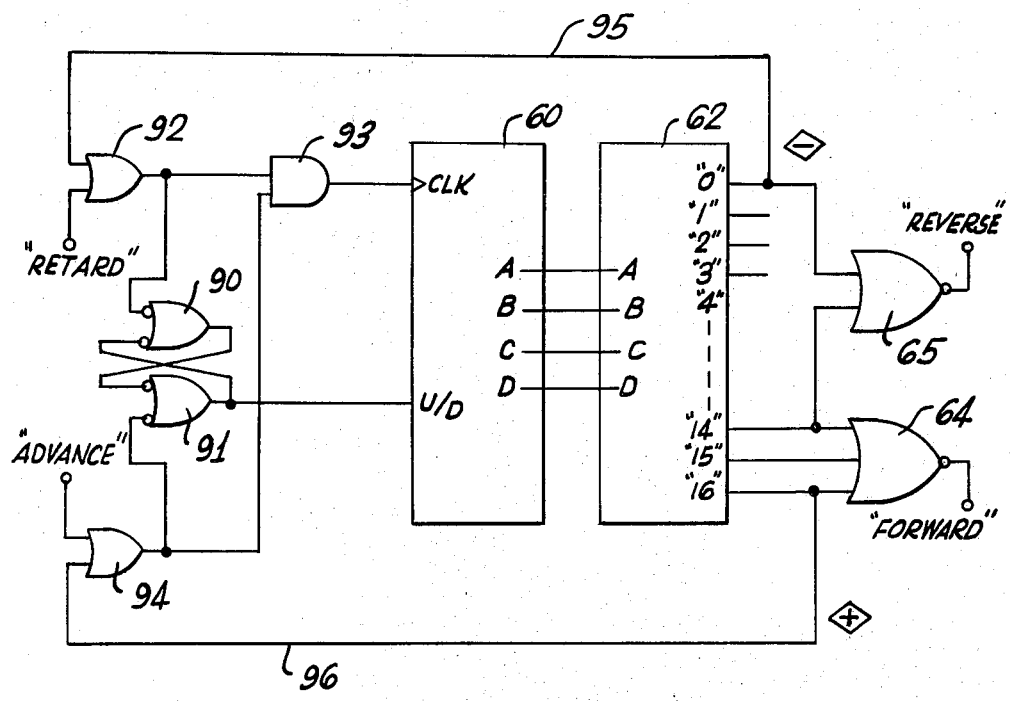
FIG. 11 illustrates suitable logic responsive to "advance" and "retard" signals to generate appropriate "reverse" and "forward" command signals and their logical complements for the motor drive subsystem of the present invention.

FIG. 11 illustrates suitable logic responsive to "retard" and "advance" signals from the logic subsystems of FIGS. 9b and 10b, respectively, to generate appropriate "reverse" and "forward" command signals and their logical complements for the motor drive subsystem, all in accordance with the invention. The up/down counter 60 and 4 to 16 line decoder 62, together with the NOR gates 64, 65 correspond to like elements in the system shown in FIG. 3.

A pair of cross-coupled NAND gates 90, 91 define a set-reset flip-flop, the output state of which conditions the "up" or "down" (U/D) input of the counter 60.

When a "retard" pulse occurs, the pulse is fed through an OR gate 92 to set the flip-flop defined by the gates 90, 91 and, in this state, the output of the flip-flop conditions the counter 60 to decrement or count down. Hence, when the "retard" pulse occurs, the "down" state will be established in the counter 60 and the "retard" pulse will also pass through gate 93 into the clocking input of the counter, so that the counter will count down by a single unit for each "retard" pulse.

The counter 60 is typically a Type 4029 binary counter manufactured by R.C.A. Corp., Somerville, N.J.

Similarly, when an "advance" pulse occurs, it will pass through OR gate 94 and reset the flip-flop defined by gates 90, 91, to condition the counter 60 to the "up" state so that it will increment. The "advance" pulse is also passed through the gate 93 to the clocking input of the counter 60, so that the counter will count up by a single unit for each "advance" pulse.

The output of the counter 60 is decoded by a decoder 62, typically a Type 4514 4 line to 16 line decoder, manufactured by R.C.A. Corp., and the cooperation between the counter 60 and counter 62 is as previously described in connection with the system of FIG. 3.

It is also desired in system of FIG. 11 that the system not attempt to count below "0" or above the maximum output state of "16". Hence, the "0" output is fed back, over line 95, as an additional input to the retard OR gate 92, thus providing a steady state d.c. signal input which prevents a clock edge from being passed by the gate 92, in the event another "retard" signal occurs which would tend to drive the counter below "0". Hence, the clocking edge from the "retard" signal is eliminated until the system is moved out of the "0" state of the decoder 62.

Similarly, the "16" output state from the decoder 62 is fed back, via line 96, to the input of the "advance" OR gate 94 to prevent the system from attempting to count above the "16" state on any "advance" signal.

FIG. 12 illustrates suitable logic for generating a 4-phase clock used to provide the clock signals for the various circuits illustrating the practice of the invention.

A pair of D flip-flops 101, 102 and four decoding AND gates 103–104 essentially define the system for generating a 4-phase clock. The pair of flip-flops 101, 102 cyclicly generate a count of "4" which is decoded out as four clock signals CLK 1, CLK 2, CLK 3, CLK 4 by the AND gates 103–106 as the system is clocked by the master clock signal CLK.

The timing diagram waveforms for the various clock signals and flip-flop states is illustrated in FIGS. 13a–13g. The master clock signal CLK is illustrated in FIG. 13a. FIGS. 13b and 13c illustrate the Q 1 and Q 2 waveform outputs from the flip-flops 101, 102, respectively, in FIG. 12. FIGS. 13d–13g are timing diagram waveforms for each of the clock signals CLK 1–CLK 4, respectively, generated from the signals Q 1, Q 2 and their logical complements $\overline{Q}$ 1 and $\overline{Q}$ 2.

The clock signals CLK 1 and CLK 2 are used for timing purposes in the position detectors and transition detectors. The clock signals CLK 3 and CLK 4 are similarly used in the transition detector 48 of FIG. 3 to latch the advance motor signal A ↑ from the waveform generated by the motor rate selection subsystem 24, in a manner similar to the transition detector of FIG. 8b, so that the pulse width of the advance motor signal A ↑ is determined by the spacing between the leading edges of the CLK 3 and CLK 4 signals. Of course, the A ↑ could be issued as a regularly occurring pulse, without extracting the signal from a waveform by means of a transition detector, without in any way affecting the invention.

Figure 14:
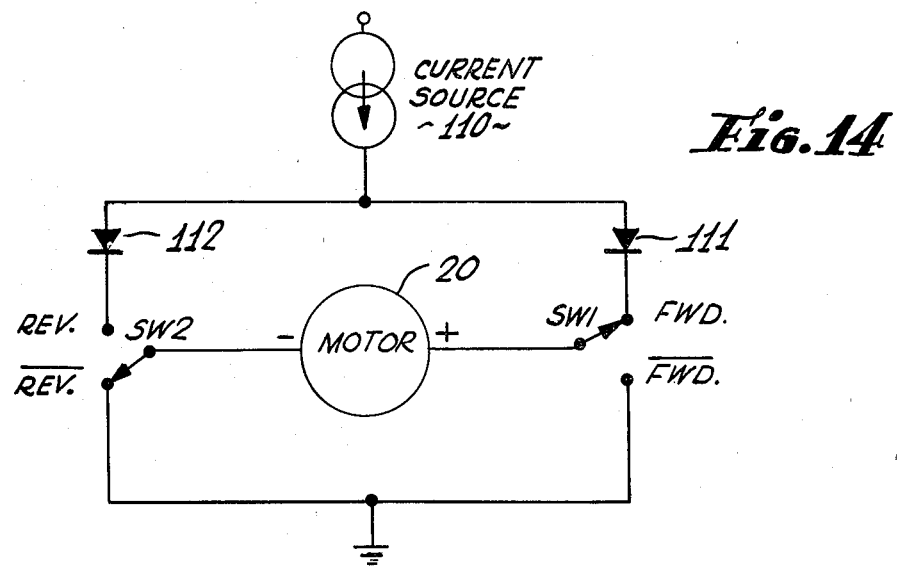
FIG. 14 is a simplified diagram of the modified H-drive used in the system of the present invention.

FIG. 14 is a simplified diagram of the modified H-drive used in the system of the present invention which provides four modes of operation of the motor, "forward", "coast", "braking" and "reverse", in response to the "forward" and "reverse" signals from the OR gates 64, 65, respectively, in FIG. 3.

The motor 20 is connected between left and right vertical legs in an H-drive configuration. The upper portion of the right leg is connected through a diode 111 to a current source 110. Similarly, the upper portion of the left leg of the H-drive is connected through a diode 112 to the source 110. The lower portions of both the left and right legs are connected to ground.

The positive and negative sides of the motor 20 are connected through switches SW 1 and SW 2, respectively, so that the motor can be selectively connected on each side to either the upper portion of the leg or to the lower portion of the leg on that same side. The position of the switch SW 1 is controlled by the "forward" signal FWD and its complement $\overline{FWD}$, whereas the position of the switch SW 2 is similarly controlled by the "reverse" signal REV and its complement $\overline{REV}$.

When the FWD and $\overline{REV}$ signals are both high, the switches SW 1 and SW 2 are in the positions shown in FIG. 14. Current passes from the source 110, through the diode 111, through the switch SW 1, into the positive end of the motor 20, out through the negative end of the motor, and through the switch SW 2 to ground. In this situation, the motor 20 will be driven forward.

If the REV and $\overline{FWD}$ signals are both high, current flow through the motor would be reversed and the motor 20 would be driven backwards.

If both the FWD and REV signals are high, so that both switches SW 1 and SW 2 are connected to the upper portions of the H-drive legs, and the motor 20 is already rotating, the motor would see an open circuit condition because of the back-to-back connected diodes 111, 112. In essence, the motor 20 would be effectively electrically disconnected, so that it would be placed in a "coast" state. Although the rotating motor 20 acts as a generator, the diodes 111, 112 prevent any current flow.

If both the $\overline{FWD}$ and $\overline{REV}$ signals are high, then both of the switches SW 1 and SW 2 are essentially in their down positions, so that the motor 20 is short-circuited to ground. Under these circumstances, the motor 20 acts as a generator while it is moving, but the short-circuit presents a very heavy load and causes the motor to slow down in the "braking" state.

Figure 15:
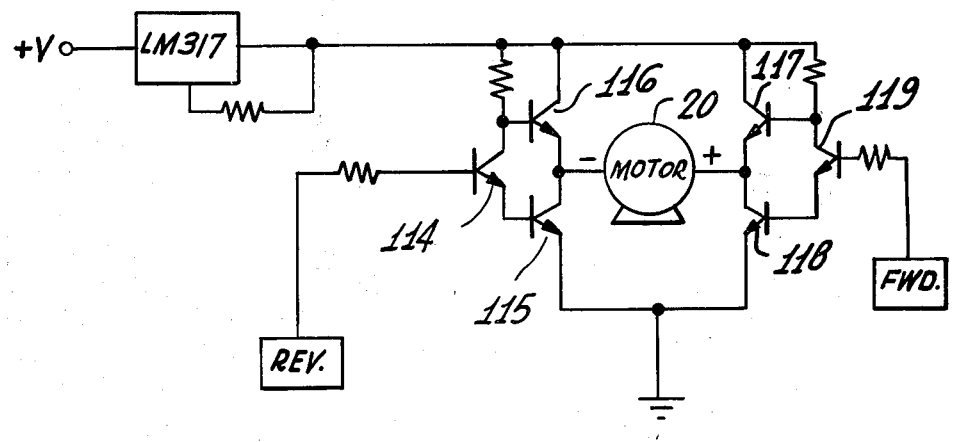
FIG. 15 is a more detailed electrical schematic of the modified H-drive used in the digital servo control system of the present invention.

FIG. 15 is a more detailed electrical schematic of the modified H-drive used in the digital servo control system of the present invention. Essentially, a Type LM 317 voltage regulator chip, manufactured by National Semiconductor Corp. of Santa Clara, Calif., is substituted for the current source 110 in FIG. 14. In addition, a plurality of solid state switches in the form of transistors 114-119 are substituted for the schematically illustrated switches SW 1 and SW 2 in FIG. 14. These transistors are typically Type PN2222 transistors manufactured by National Semiconductor Corp. The emitter-base junctions of the transistors 116, 117 replace the diodes 111, 112 in FIG. 14 and perform the same function.

The new and improved digital servo motor control system of the present invention, suitable for use as a motor drive in an IV syringe pump or the like, is extremely accurate, reliable and easy to use in selecting and maintaining fluid flow rates over an extremely wide operational range, in a system which is more compact, less expensive, requires fewer electronic components and has lower power requirements. The d.c. motor 20 performs with stepping motor precision over a much wider speed range than a typical stepping motor or a conventional d.c. motor and does so over widely varying load conditions.

It will be apparent from the foregoing that, while particular forms of the invention have been illustrated and described, various modifications can be made without departing from the spirit and scope of the invention. Accordingly, it is not intended that the invention be limited, except as by the appended claims.

We claim:

1. In a motor control system, the combination comprising:

a d.c. motor;

first means for sensing motor position and direction, said first means including a disc rotating synchronously with rotation of the motor, said disc having alternating light and dark sectors, and a pair of photosensors monitoring said disc as it rotates;

second means for selectively establishing a desired motor rate;

third means, responsive to both said first means and said second means, to generate motor "advance" and motor "retard" information regarding the status of motor performance, said third means including an advance and retard logic means in accordance with the Boolean equations:

ADVANCE LOGIC $= \overline{C}(B\downarrow) + C(B\uparrow) + B(C\downarrow) + \overline{B}(C\uparrow) + A\uparrow$ RETARD LOGIC $= C(B\downarrow) + \overline{C}(B\uparrow) + B(C\uparrow) + \overline{B}(C\downarrow)$ where:

B = response to a light sector in one of said pair of photosensors, $\overline{B}$ = response to a dark sector in said one of said pair of photosensors, C = response to a light sector in the other of said pair of photosensors, $\overline{C}$ = response to a dark sector in said other of said pair of photosensors, B ↑ = sensor change from light to dark in said one of said pair of photosensors, B ↓ = sensor change form dark to light in said one of said pair of photosensors, C ↑ = sensor change from light to dark in said other of said pair of photosensors, C ↓ = sensor change from dark to light in said other of said pair of photosensors, A ↑ = occurrence of an advance motor signal; and fourth means, responsive to said third means, for selectively driving said motor at any one time in a selected mode from a hierarchy of four different modes of operation including forward movement, coasting movement, braking of movement, and reverse movement, whereby said motor movement can be accurately controlled over a wider speed control range.

2. A combination as set forth in claim 1, wherein said photosensors are in phase quadrature, spaced ½ of a single sector apart along said disc.

3. A system as set forth in claim 2, wherein said fourth means includes a counting means which is incremented and decremented by said third means to vary the mode of operation of the motor from said hierarchy.

4. A system as set forth in claim 2, wherein said fourth means includes:
  a counting means selectively incremented and decremented by said advance and retard logic; and
  decoder means to vary the mode of operation of the motor from said hierarchy in accordance with the state of said counting means.

5. In a digital servo control system for a d.c. motor, the combination comprising:
  first means for providing signals indicative of motor position and direction, said first means including a disc rotating synchronously with rotation of the motor, said disc having alternating light and dark sectors and a pair of photosensors for monitoring the position and direction of movement of said disc as it rotates past said photosensors;
  second means for providing advance motor signals at a desired motor rate;
  third means, responsive to said first means and said second means, for accumulating information regarding the actual position of the motor relative to where the motor should be at any point in time, said third means including an advance and retard logic means in accordance with the Boolean equations:

ADVANCE
   LOGIC $= \overline{C}(B\downarrow) + C(B\uparrow) + B(C\downarrow) + \overline{B}(C\uparrow) + A\uparrow$ RETARD
   LOGIC $= C(B\downarrow) + \overline{C}(B\uparrow) + B(C\uparrow) + \overline{B}(C\downarrow)$ where:
  B = response to a light sector in one of said pair of photosensors,
  $\overline{B}$ = response to a dark sector in said one of said pair of photosensors,
  C = response to a light sector in the other of said pair of photosensors,
  $\overline{C}$ = response to a dark sector in said other of said pair of photosensors,
  B ↑ = sensor change from light to dark in said one of said pair of photosensors,
  B ↓ = sensor change from dark to light in said one of said pair of photosensors,
  C ↑ = sensor change from light to dark in said other of said pair of photosensors,
  C ↓ = sensor change from dark to light in said other of said pair of photosensors,
  A ↑ = occurrence of an advance motor signal; and
  fourth means, responsive to the changing state of said third means, for generating motor drive signals to establish different modes of operation of the motor from a prescribed hierarchy.

6. A system as set forth in claim 5, wherein said fourth means includes:
  a counting means selectively incremented and decremented by said advance and retard logic means; and
  decoder means to vary the mode of operation of the motor from said hierarchy in accordance with the state of said counting means.

7. In a digital servo control system for a d.c. motor, the combination comprising:
  first means for providing signals indicative of motor position and direction;
  second means for providing advance motor signals at a desired motor rate;
  third means, responsive to said first means and said second means, for accumulating information regarding the actual position of the motor relative to where the motor should be at any point in time; and
  fourth means, responsive to the changing state of said third means, for generating motor drive signals to establish different modes of operation of the motor from a prescribed hierarchy, said fourth means including a counting means which is incremented and decremented by said third means to vary the mode of operation of the motor from said prescribed hierarchy.

8. In a motor control system, the combination comprising:
  a d.c. motor;
  first means for sensing motor position and direction;
  second means for selectively establishing a desired motor rate;
  third means, responsive to both said first means and said second means, to generate motor "advance" and motor "retard" information regarding the status of motor performance;
  fourth means, responsive to said third means, for selectively driving said motor at any one time in a selected mode from a hierarchy of four different modes of operation including forward movement, coasting movement, braking of movement, and reverse movement, whereby said motor movement can be accurately controlled over a wider speed control range; said fourth means including switching means for selectively switching said motor and applying electrical power to:
    (a) drive the motor in the forward direction,
    (b) drive the motor in the reverse direction,
    (c) connect a high impedance across the motor to cause the motor to coast,
    (d) short-circuit the motor to cause the motor to slow down in a braking mode.

9. A method of controlling a d.c. motor for quasi-incremental movement over a wide speed control range, comprising steps of:
  selecting a motor rate;
  monitoring actual movement of the motor to determine the cumulative status of the motor regarding the actual position of the motor relative to where the motor should be at any point in time; and
  selectively switching the motor and applying electrical power to:
    (a) drive the motor in a forward direction,
    (b) drive the motor in a reverse direction,
    (c) connect a high impedance across the motor to cause the motor to coast, (d) short-circuit the motor to cause the motor to slow down in a braking mode.

10. In a motor control system, the combination comprising:
- a d.c. motor; and
- switching means for selectively switching said motor and applying electrical power to:
    - (a) drive said motor in a forward direction,
    - (b) drive said motor in a reverse direction,
    - (c) connect a high impedance across said motor to cause said motor to coast,
    - (d) short-circuit said motor to cause said motor to slow down in a braking mode.

11. A combination as set forth in claim 10 wherein said switching means includes solid state switches.

12. A combination as set forth in claim 11, wherein said switching means is conditioned by "reverse" and "forward" signals and their complements.

13. A digital servo control system for a d.c. motor, comprising:
- first means for monitoring lagging and leading movement of the motor;
- second means, responsive to said first means, for establishing a hierarchy of modes of operation of the motor, whereby said motor can be commanded to move forward, coast, brake or move in reverse; and
- third means, responsive to said second means, for selectively switching the motor and applying electrical power to:
    - (a) drive said motor in the forward direction;
    - (b) drive said motor in the reverse direction;
    - (c) connect a high impedance across said motor to cause said motor to coast;
    - (d) short-circuit said motor to cause said motor to slow down in a braking mode, whereby the motor movement can be accurately controlled over a wider speed control range.

14. A control system as set forth in claim 13, wherein said third means includes solid state switching means.

* * * * *

UNITED STATES PATENT AND TRADEMARK OFFICE
CERTIFICATE OF CORRECTION

PATENT NO. : 4,367,435

DATED : January 4, 1983

INVENTOR(S) : Wilber H. Bailey, Stephen J. Kreinick & Bradley J. Denny

It is certified that error appears in the above-identified patent and that said Letters Patent is hereby corrected as shown below:

Column 4, line 37, delete "emobodying" and insert therefor --embodying--.

line 39, delete "of" and insert therefor --to--.

Column 8, line 54, delete "a" and insert therefor --an--.

Column 9, line 11, delete "B" and insert therefor --$\overline{B}$--.

line 30, after "C(B↓)", insert therein --signal combination, followed by B(C↑) and $\overline{C}$(B↑)--.

line 67, delete "are" and insert therefor --is--.

Column 10, line 18, delete "common" and insert therefor --command--.

Column 11, line 16, delete "as as" and insert therefor --as--.

line 21, delete "corresponds" and insert therefor --correspond--.

UNITED STATES PATENT AND TRADEMARK OFFICE
CERTIFICATE OF CORRECTION

PATENT NO. : 4,367,435

DATED : January 4, 1983

INVENTOR(S) : Wilber H. Bailey, Stephen J. Kreinick & Bradley J. Denny

It is certified that error appears in the above-identified patent and that said Letters Patent is hereby corrected as shown below:

Column 11, line 23, delete "will be both" and insert therefor --will both--.

line 42, delete "and Q" and insert therefor --$\overline{Q}$--.

Column 14, line 63, delete "form" and insert therefor --from--.

Signed and Sealed this

Twenty-second Day of May 1984

[SEAL]

Attest:

GERALD J. MOSSINGHOFF

*Attesting Officer*  *Commissioner of Patents and Trademarks*